United States Patent
Jouanneau et al.

(10) Patent No.: US 11,434,188 B2
(45) Date of Patent: Sep. 6, 2022

(54) METHOD FOR MANUFACTURING 1,4-BIS (4-PHENOXYBENZOYL)BENZENE AT AN ELEVATED TEMPERATURE

(71) Applicant: Arkema France, Colombes (FR)

(72) Inventors: Julien Jouanneau, King of Prussia, PA (US); Guillaume Le, Serquigny (FR); Martin Herblot, Serquigny (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 17/291,679

(22) PCT Filed: Nov. 7, 2019

(86) PCT No.: PCT/EP2019/080623
§ 371 (c)(1),
(2) Date: May 6, 2021

(87) PCT Pub. No.: WO2020/094818
PCT Pub. Date: May 14, 2020

(65) Prior Publication Data
US 2021/0363088 A1 Nov. 25, 2021

(30) Foreign Application Priority Data
Nov. 9, 2018 (EP) .................... 18306471

(51) Int. Cl.
*C07C 41/00* (2006.01)
*C07C 45/46* (2006.01)

(52) U.S. Cl.
CPC .................... *C07C 45/46* (2013.01)

(58) Field of Classification Search
CPC ................ C07C 41/36; C08G 2650/40
See application file for complete search history.

(56) References Cited

U.S. PATENT DOCUMENTS

| | | | |
|---|---|---|---|
| 4,704,448 A | 11/1987 | Brugel | |
| 4,709,007 A | 11/1987 | Jansons et al. | |
| 4,716,211 A | 12/1987 | Clendinning et al. | |
| 4,794,155 A | 12/1988 | Woo et al. | |
| 4,816,556 A | 3/1989 | Gay et al. | |
| 4,826,947 A | 5/1989 | Jansons et al. | |
| 4,827,041 A | 5/1989 | Ford et al. | |
| 4,835,319 A | 5/1989 | Corbin et al. | |
| 4,891,167 A | 1/1990 | Clendinning et al. | |
| 4,918,237 A * | 4/1990 | Corbin et al. ....... | C07C 49/84 568/322 |
| 4,931,530 A | 6/1990 | Fukuwa et al. | |
| 5,137,988 A | 8/1992 | Matzner et al. | |
| 5,258,491 A | 11/1993 | Agreda et al. | |
| 5,734,005 A | 3/1998 | Daniels et al. | |
| 10,344,125 B2 | 7/2019 | Le et al. | |
| 10,428,002 B2 | 10/2019 | Jouanneau et al. | |
| 10,611,715 B2 | 4/2020 | Jouanneau et al. | |
| 10,618,863 B2 | 4/2020 | Jouanneau et al. | |
| 10,793,500 B2 | 10/2020 | Jouanneau et al. | |
| 10,807,933 B2 | 10/2020 | Le et al. | |
| 10,981,852 B2 | 4/2021 | Jouanneau et al. | |
| 2015/0183918 A1 | 7/2015 | Le et al. | |
| 2018/0334418 A1 | 11/2018 | Jouanneau et al. | |
| 2018/0334419 A1 | 11/2018 | Jouanneau et al. | |
| 2018/0334420 A1 | 11/2018 | Le et al. | |
| 2018/0334538 A1 | 11/2018 | Le et al. | |
| 2019/0040189 A1 | 2/2019 | Le et al. | |
| 2019/0077739 A1 | 3/2019 | Jouanneau et al. | |
| 2019/0135721 A1 | 5/2019 | Jouanneau et al. | |
| 2019/0152886 A1 | 5/2019 | Jouanneau et al. | |
| 2020/0062683 A1 | 2/2020 | Jouanneau et al. | |
| 2020/0079717 A1 | 3/2020 | Le et al. | |

(Continued)

FOREIGN PATENT DOCUMENTS

| | | |
|---|---|---|
| EP | 0 192 260 A1 | 8/1986 |
| EP | 0 268 112 A2 | 5/1988 |

(Continued)

OTHER PUBLICATIONS

International Search Report (PCT/ISA/210) and Written Opinion (PCT/ISA/237) dated Jan. 22, 2020, by the European Patent Office as the International Searching Authority for International Application No. PCT/EP2019/080623. (9 pages).
U.S. Appl. No. 15/982,625, Guillaume Le and Julien Jouanneau, filed May 17, 2018, (Cited herein as US Patent Application Publication No. 2018/0334420 A1 of Nov. 22, 2018).
U.S. Appl. No. 16/613,454, Julien Jouanneau, Jérôme Amstutz and Guillaume Vincent, filed Nov. 14, 2019, (Cited herein as US Patent Application No. 2021/0155570 A1 of May 27, 2021).
European Search Report in application No. EP 17305559.1, dated Nov. 9, 2017, European Patent Office, Munich, DE, 10 pages.
International Search Report and Written Opinion, issued in PCT/EP2018/062803, dated Jul. 12, 2018, European Patent Office, Rijswijk, NL, 10 pages.

(Continued)

*Primary Examiner* — Sikarl A Witherspoon
(74) *Attorney, Agent, or Firm* — Buchanan Ingersoll & Rooney P.C.

(57) ABSTRACT

A method for manufacturing 1,4-bis(4-phenoxybenzoyl) benzene, including: providing a solvent, a Lewis acid, a first reactant and a second reactant, wherein the first reactant and the second reactant are respectively terephthaloyl chloride and diphenyl ether, or reversely; mixing the first reactant in the solvent to make a starting mixture; and, adding the second reactant to the starting mixture; wherein the Lewis acid is mixed, at least partly, to the starting mixture before adding the second reactant to the starting mixture, and/or wherein the Lewis acid is mixed, at least partly, with the second reactant and added together to the starting mixture, and wherein the temperature of the starting mixture is greater than 5° C. during at least part of the step of adding the second reactant to the starting mixture; so as to obtain a product mixture comprising a 1,4-bis(4-phenoxybenzoyl) benzene-Lewis acid complex.

16 Claims, No Drawings

(56) References Cited

U.S. PATENT DOCUMENTS

| | | |
|---|---|---|
| 2020/0087456 A1 | 3/2020 | Le et al. |
| 2020/0109100 A1 | 4/2020 | Jouanneau et al. |
| 2021/0155570 A1 | 5/2021 | Jouanneau et al. |
| 2021/0155571 A1 | 5/2021 | Le et al. |

FOREIGN PATENT DOCUMENTS

| | | |
|---|---|---|
| EP | 0 298 771 A2 | 1/1989 |
| EP | 0316133 A2 | 5/1989 |
| EP | 0 268 112 A3 | 11/1989 |
| EP | 0 268 112 B1 | 3/1994 |
| EP | 3 438 085 A1 | 2/2019 |
| GB | 2 287 031 A | 9/1995 |
| IN | 193687 | 7/2004 |
| JP | S61-195122 A | 8/1986 |
| JP | S61-211336 A | 9/1986 |
| JP | S63-258923 A | 10/1988 |
| JP | S64-038435 A | 2/1989 |
| JP | H01-163149 A | 6/1989 |
| JP | H04-503517 A | 6/1992 |
| SU | 445 643 A | 12/1975 |
| SU | 638588 | 12/1978 |
| SU | 626555 A1 | 7/1979 |
| WO | 9523821 A1 | 9/1995 |
| WO | WO 2020/094819 A1 | 5/2020 |

OTHER PUBLICATIONS

European Search Report in application No. EP 17305561.7, dated Nov. 3, 2017, European Patent Office, Munich, DE, 5 pages.
International Search Report and Written Opinion, issued in PCT/EP2018/062796, dated Aug. 20, 2018, European Patent Office, Rijswijk, NL, 7 pages.
European Search Report in application No. EP 17305562.5, dated Dec. 6, 2017, European Patent Office, Munich, DE, 10 pages.
International Search Report and Written Opinion, issued in PCT/EP2018/062813, dated Jun. 29, 2018, European Patent Office, Rijswijk, NL, 11 pages.
European Search Report in application No. EP 17305581.5, dated Nov. 24, 2017, European Patent Office, Munich, DE, 6 pages.
International Search Report and Written Opinion, issued in PCT/EP2018/063013, dated Jul. 24, 2018, European Patent Office, Rijswijk, NL, 8 pages.
European Search Report in application No. EP 17305582.3, dated Nov. 8, 2017, European Patent Office, Munich, DE, 7 pages.
International Search Report and Written Opinion, issued in PCT/EP2018/063017, dated Jul. 4, 2018, European Patent Office, Rijswijk, NL, 9 pages.
European Search Report in application No. EP 17305583.1, dated Aug. 22, 2017, European Patent Office, Munich, DE, 8 pages.
International Search Report and Written Opinion, issued in PCT/EP2018/063014, dated Jul. 24, 2018, European Patent Office, Rijswijk, NL, 10 pages.
European Search Report in Application No. EP 18306471.6, dated May 17, 2019, European Patent Office, Munich, DE, 7 pages.
International Search Report and Written Opinion issued in PCT/EP2019/080623, dated Jan. 22, 2020, European Patent Office, Rijswijk, NL, 9 pages.
European Search Report in application No. EP 18306473.2, dated Apr. 18, 2019, European Patent Office, Munich, DE, 5 pages.
International Search Report and Written Opinion issued in PCT/EP2019/080625, dated Jan. 20, 2020, European Patent Office, Rijswijk, NL, 7 pages.
International Search Report and Written Opinion issued in PCT/EP2019/080624, dated Feb. 12, 2020, European Patent office, Rijswijk, NL, 10 pages.
Database WPI Week 197630, AN 1976-57263X, Dec. 19, 1975, vol. 1976, No. 30,31, 1 page, Thomson Scientific, London, GB (XP002775200).
Banihashemi, Ahmad, et al., "New heat stable polyethers, polyketones and polysulfones", *Macromolecular Chemistry and Physics*, vol. 200, No. 10, Oct. 1, 1999, pp. 2284-2293, Wiley-VCH Verlag GmbH, Weinheim, DE (XP055420800).
Baysec, Sebnem, et al., "Very High Solid State Photoluminescence Quantum Yields of Poly(tetraphenylethylene) Derivatives", *Macromolecular Rapid Communications*, vol. 37, No. 22, Sep. 26, 2016, pp. 1802-1806, Wiley-VCH Verlag GmbH & Co. KgaA, Weinheim, DE (XP055420789).
Brown, R. R., et al., "Solubility and Activity of Aluminum Chloride in Aqueous Hydrochloric Acid Solutions," *RI 8379—Bureau of Mines Report of Investigations/1979*, 1979, United States Department of the Interior, Reproduced by National Technical Information Service, U.S. Department of Commerce, Springfield, VA 22161, 26 pages.
Fukawa, Isaburo, et al., "Preparation of Dibenzofuran-Type Amorphous Polyetherketone by Novel Etherification Reaction", *Journal of Polymer Science: Part A: Polymer Chemistry*, Jan. 1, 1992, pp. 1977-1985, vol. 30 (XP055420842).
March, Jerry, "Advanced Organic Chemistry", Dec. 31, 1985, p. 333, copyright page, John Wiley & Sons, New York (XP002775202).
Mithyantha, et al. , "A process for the purification of 1,4-bis(4-phenoxybenzoyl)benzene", Database CAPLUS [Online], Aug. 23, 2006, 1 page, Chemical Abstracts Service, Columbus, OH, Database accession No. 2006:838198 (XP002775201).
Stevens, G.W., et al., "Extraction, Liquid-Liquid," *Kirk-Othmer Encyclopedia of Chemical Technology*, 2007, pp. 1-62, John Wiley & Sons, Inc., NJ, United States (published online Jun. 15, 2007).
Streitwieser, Andrew, et al. , "Introduction to Organic Chemistry", Dec. 31, 1981, p. 544, copyright page, MacMillan Publishing Co., Inc., New York (XP002775203).
Zolotukhin, et al., "Aromatic polymers obtained by precipitation polycondensation: 4*. Synthesis of poly(ether ketone ketone)s," *Polymer*, 1997, pp. 1471-1476, vol. 38, No. 6, Elsevier, GB.
Notice of Reasons for Rejection dated Jun. 29, 2020 in Japanese Patent Application No. 2019-563523, Japan Patent Office, JP, 5 pages including English-language translation.
Official Action and Search Report dated Apr. 3, 2020 in RU Application No. 2019141274/04(080650), Federal Service for Intellectual Property, Federal Institute of Industrial Property (FIPS), Moscow, RU, 6 pages.
Notice of Reasons for Rejection dated Jun. 29, 2020 in Japanese Patent Application No. 2019-563519, Japan Patent Office, JP, 12 pages including English-language translation.
Official Action and Search Report dated Mar. 31, 2020 in RU Application No. 2019141830/04(081574), Federal Service for Intellectual Property, Federal Institute of Industrial Property (FIPS), Moscow, RU, 6 pages.
Official Action (English-language translation) dated Apr. 2, 2021 in Chinese Patent Application No. 201880032786.1, China National Intellectual Property Administration, Beijing, CN, 10 pages.

* cited by examiner

METHOD FOR MANUFACTURING 1,4-BIS (4-PHENOXYBENZOYL)BENZENE AT AN ELEVATED TEMPERATURE

TECHNICAL FIELD

The present application relates to a method for manufacturing 1,4-bis(4-phenoxybenzoyl)benzene, as well as polyaryl etherketone polymers, in particular polyether ketone ketone polymers, starting from said 1,4-bis(4-phenoxybenzoyl)benzene.

TECHNICAL BACKGROUND

Polyether ketone ketone (PEKK) polymers have a number of properties which make them useful in applications involving exposure to high temperature or to high mechanical or chemical stress. They are, for instance, useful in the aerospace industry, in off-shore drilling and in medical devices.

One known route for manufacturing polyether ketone ketone polymers relies on the use of 1,4-bis(4-phenoxybenzoyl)benzene as a starting material.

1,4-bis(4-phenoxybenzoyl)benzene can be prepared by reacting terephthaloyl chloride and diphenyl ether in the presence of a Lewis acid, such as aluminum trichloride.

In document U.S. Pat. No. 4,816,556 (example 2), 1,4-bis(4-phenoxybenzoyl)benzene is prepared by dissolving terephthaloyl chloride and diphenyl ether in ortho-dichlorobenzene, cooling to 0-5° C. and adding aluminum chloride with temperature kept below 5° C. The mixture is then warmed to 20° C. Thereafter, cold methanol is added so as to produce a slurry which is filtered, reslurried in methanol and filtered again.

In document U.S. Pat. No. 4,826,947 (example 2), 1,4-bis(4-phenoxybenzoyl)benzene is prepared by providing a mixture of methylene chloride, methylsulfone and aluminum trichloride, cooling to a temperature of between −30 and −35° C., and then adding diphenyl ether and thereafter terephthaloyl chloride. The reaction mixture is then poured into cold methanol so as to make a slurry which is then filtered.

Document WO 95/23821 (example 11) discloses providing aluminum chloride in ortho-dichlorobenzene cooled in an ice bath, and then adding terephthaloyl chloride and diphenyl ether. Thereafter, the reaction mixture is allowed to warm up to room temperature, stirred, and poured into a methanol concentrated HCl solution. A precipitate is formed which is subsequently filtered off.

There is still a need for new methods for manufacturing 1,4-bis(4-phenoxybenzoyl)benzene with a high purity and a high yield, which can be implemented at the industrial scale in an economically realistic manner.

SUMMARY

It is an object of the invention to provide a method for manufacturing 1,4-bis(4-phenoxybenzoyl)benzene, comprising:
  providing a solvent, a Lewis acid, a first reactant and a second reactant,
  wherein the first reactant and the second reactant are respectively terephthaloyl chloride and diphenyl ether, or reversely;
  mixing the first reactant in the solvent to make a starting mixture; and,
  adding the second reactant to the starting mixture;
  wherein the Lewis acid is mixed, at least partly, to the starting mixture before adding the second reactant to the starting mixture, and/or
  wherein the Lewis acid is mixed, at least partly, with the second reactant and added together to the starting mixture, and
  wherein the temperature of the starting mixture is greater than 5° C. during at least part of the step of adding the second reactant to the starting mixture.

A product mixture comprising a 1,4-bis(4-phenoxybenzoyl)benzene-Lewis acid complex is obtained.

The Lewis acid is chosen among the list consisting of: aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride.

In some embodiments, the Lewis acid is chosen among the list consisting of: aluminum trichloride, boron trichloride, aluminum tribromide, titanium tetrachloride, antimony pentachloride, ferric chloride, gallium trichloride, and molybdenum pentachloride.

In some embodiments, the Lewis acid is aluminum trichloride.

In some embodiments, the temperature of the starting mixture is at least 15° C., preferably at least 25° C., or at least 35° C. or at least 45° C., or at least 55° C., or at least 60° C., or at least 65° C., or at least 75° C., or at least 85° C., or at least 95° C., or at least 100° C., or at least 110° C., or about 120° C., during at least part of the step of adding the second reactant to the starting mixture.

In some embodiments, the temperature of the starting mixture is at least 30° C., preferably at least 40° C., or at least 45° C., or at least 50° C., or at least 55° C., or at least 60° C., or at least 65° C., or at least 75° C., or at least 85° C., or at least 95° C., or at least 100° C., or at least 110° C., or about 120° C., after 20% by weight of the second reactant has been added to the starting mixture, relative to the total weight of the second reactant added to the starting mixture.

In some embodiments, the temperature of the starting mixture increases during the step of adding the second reactant to the starting mixture, from an initial temperature to a final temperature.

In some embodiments, the initial temperature of the starting mixture is from 0 to 120° C., preferably from 0 to 80° C., and more preferably from 30° C. to 50° C.

In some embodiments, the final temperature is at least 30° C., preferably at least 40° C., or at least 45° C., or at least 50° C., or at least 55° C., or at least 60° C., or at least 65° C., or at least 75° C., or at least 85° C., or at least 95° C., or at least 100° C., or at least 110° C., or about 120° C.

In some embodiments, the temperature of the starting mixture does not exceed 180° C., preferably does not exceed 120° C., preferably does not exceed 100° C., more preferably does not exceed 80° C., even more preferably does not exceed 70° C., during the step of adding the second reactant.

In some embodiments, the temperature difference between the final temperature and the initial temperature is from 1 to 120° C., preferably from 1 to 70° C., preferably from 5 to 60° C., more preferably from 10 to 50° C., and in particular from 20 to 40° C.

In some embodiments, the solvent is a separate solvent from the diphenyl ether, the terephthaloyl chloride, or the Lewis acid. In particular, the solvent can be ortho-dichlorobenzene.

On the contrary, in some other embodiments the solvent is either diphenyl ether, terephthaloyl chloride or the Lewis acid.

In some embodiments, the second reactant is terephthaloyl chloride. The Lewis acid is mixed to terephthaloyl chloride and added together to the starting mixture.

In some embodiments, the second reactant is terephthaloyl chloride and the Lewis acid is mixed to the starting mixture before adding the terephthaloyl chloride to the starting mixture.

In some embodiments, the concentration by weight of terephthaloyl chloride (relative to a sum by weight of the solvent, the terephthaloyl chloride, the diphenyl ether and the Lewis acid) is from 2 to 25%, preferably from 3 to 12%, and more preferably from 5 to 10%.

In some embodiments, the concentration by weight of diphenyl ether (relative to a sum by weight of the solvent, the terephthaloyl chloride, the diphenyl ether and the Lewis acid) is from 2 to 42%, preferably from 5 to 35%, and more preferably from 12 to 25%.

In some embodiments, the weight ratio of terephthaloyl chloride to diphenyl ether introduced into the reactor is from 0.05 to 0.6, preferably from 0.2 to 0.6, and more preferably from 0.3 to 0.5.

In some embodiments, the method of embodiments of the invention comprises one or more steps for purifying 1,4-bis(4-phenoxybenzoyl)benzene-Lewis acid complex from the product mixture.

Another object of the invention is a method of making a polyether ketone ketone polymer, comprising:
manufacturing 1,4-bis(4-phenoxybenzoyl)benzene according to the method described above;
reacting said 1,4-bis(4-phenoxybenzoyl)benzene with at least one difunctional aromatic acyl chloride.

The present invention provides a method for manufacturing 1,4-bis(4-phenoxybenzoyl)benzene with good productivity, a high purity and/or a high yield. This method can be implemented at the industrial scale.

DETAILED DESCRIPTION OF EMBODIMENTS

Embodiments of the invention will now be described in more detail without limitation in the following description.

1,4-bis(4-phenoxybenzoyl)benzene (abbreviated name: EKKE) is the compound of formula I:

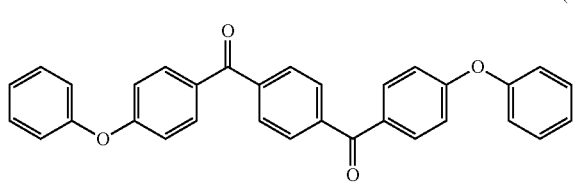

It may be made by reacting together terephthaloyl chloride and diphenyl ether, hereafter called "first reactant" and "second reactant". In some embodiment the first reactant is terephthaloyl chloride and the second reactant is diphenyl ether. On the contrary, in other embodiments, the first reactant is diphenyl ether and the second reactant is terephthaloyl chloride.

Terephthaloyl chloride is of formula II:

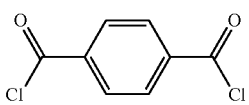

Diphenyl ether of formula III:

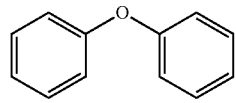

The reaction is carried out in a solvent, and in the presence of a Lewis acid, acting as a Friedel-Crafts catalyst.

The reaction results in the production of the compound of formula I which is predominantly in the form of a complex with the Lewis acid.

It is believed that the reaction comprises two stages. In the first stage, one molecule of formula II reacts with one molecule of formula III to form the intermediate 4-(4-phenoxybenzoyl)benzoyl chloride of formula IV, which is called an "active intermediate":

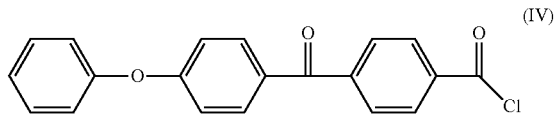

Then, one molecule of the active intermediate of formula IV reacts with another molecule of formula III to form the desired product of formula I.

During the reaction, 4-(4-phenoxybenzoyl)benzoic acid of formula IVa can also be produced to some extent (notably from the active intermediate of formula IV):

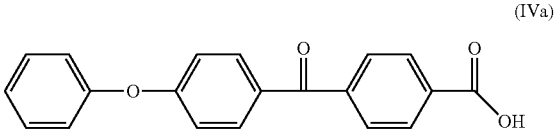 [SMILES: O=C(O)c1ccc(C(=O)c2ccc(Oc3ccccc3)cc2)cc1]

The corresponding 4-(4-phenoxybenzoyl)benzoic acid ester can be formed either directly from the acyl chloride of formula IV or from the carboxylic acid of formula IVa. The acid form and/or the ester form of the intermediate can be formed during the reaction but they can also primarily be formed from the remaining active intermediate during subsequent workup.

The 4-(4-phenoxybenzoyl)benzoic acid and 4-(4-phenoxybenzoyl)benzoic acid ester are inactive and therefore remain as impurities in the product mixture.

The other main impurities produced by the reaction are xanthydrol moiety-containing molecules of formula (V):

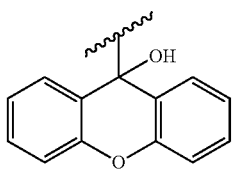

In some embodiments, one of the two reactants or the Lewis acid can play the role of the solvent.

On the opposite, in other embodiments, the solvent can be a separate solvent from the diphenyl ether, the terephthaloyl chloride, or the Lewis acid. In these embodiments, the solvent is preferably a non-protic solvent, that is to say the solvent is not a protic solvent. A "protic solvent" is a solvent containing at least one hydrogen atom bound to an oxygen or nitrogen atom, and which is therefore able to donate protons to reagents. The solvent can in particular be selected from methylene chloride, carbon disulfide, ortho-dichlorobenzene, meta-dichlorobenzene, para-dichlorobenzene, 1,2,4-trichlorobenzene, 1,2,3-trichlorobenzene, ortho-difluorobenzene, 1,2-dichloroethane, 1,1-dichloroethane, 1,1,2,2-tetrachloroethane, tetrachloroethylene, dichloromethane, nitrobenzene and mixtures thereof.

Ortho-dichlorobenzene is the most preferred solvent.

The reaction between the two reactants of formulas II and III, to make the compound of formula I may be performed in a glass reactor, a glass-lined reactor or a stainless-steel reactor.

According to some variations, the materials introduced into the reactor in the method of embodiments of the invention consist essentially, or consist, of the compounds of formulas II and III, the solvent and the Lewis acid.

According to embodiments of the invention, a starting mixture comprising the first reactant in a solvent, preferably in a separate solvent, is provided as a first step. In specific embodiments, the solvent is introduced prior to the first reactant into the reactor.

As a second step, the second reactant is added to the starting mixture.

The Lewis acid can be mixed to the starting mixture at the first step, or added to the starting mixture at the second step, or even part of the Lewis acid can be mixed to the starting mixture at the first step and part of the Lewis acid can be added to the starting mixture at the second step.

This two-step addition of the two reactants enables to obtain 1,4-bis(4-phenoxybenzoyl)benzene-Lewis acid complex, and therefore 1,4-bis(4-phenoxybenzoyl)benzene, with a high purity and a high yield, in an efficient way. In particular, it enables to avoid any prior contacting time between the two reactants as in the methods of the prior art, in which the two reactants have to be first mixed together for several hours and heated, before adding the Lewis acid. It also enables to reduce the production of unwanted by-products such as 4-(4-phenoxybenzoyl)benzoic acid or 4-(4-phenoxybenzoyl)benzoic acid ester.

In some embodiments, terephthaloyl chloride can be the second reactant. In these embodiments the diphenyl ether is therefore the first reactant, which is mixed in the solvent to make the starting mixture. The advantage to add terephthaloyl chloride as the second reactant to the starting mixture is that it enables to reduce the excess amount of the Lewis acid compared to the amount of terephthaloyl chloride introduced into the reactor. It also enables to reduce the excess amount of diphenyl ether compared to the amount of terephthaloyl chloride introduced into the reactor. Terephthaloyl chloride can be added in its solid form or in its liquid form. Alternatively, it can also be added as a suspension or a colloid, namely as a heterogeneous mixture of solid particles of terephthaloyl chloride in a solvent. The solvent for the suspension/colloid is advantageously the abovementioned reaction solvent. Alternatively, it can also be added as a solution, namely as a homogeneous mixture of liquid terephthaloyl chloride in a solvent. The solvent for the solution is preferably the abovementioned reaction solvent.

In some embodiments, terephthaloyl chloride can be the first reactant. In these embodiments, the diphenyl ether is therefore the second reactant, which is added to the starting mixture. The advantage to use the diphenyl ether as the second reactant is that it has a relatively low fusion temperature (26.9° C.) and can therefore be easily added in its liquid form at a temperature which is close to the ambient temperature. Hence, the diphenyl ether can be added very precisely to the starting mixture. Alternatively, the diphenyl ether can be added to the starting mixture as a solution in a solvent, preferably in the abovementioned solvent. In less preferred embodiments, diphenyl ether is added as a solid, or as a suspension or a colloid in a solvent, preferably in the abovementioned reaction solvent.

The Lewis acid can be a solid. In some variations, the Lewis acid can be in a particulate form, such as in the form of granules (having, e.g., a Dv80 of more than 1 mm) or in the form of a powder (having, e.g., a Dv80 of less than 1 mm, and preferably a Dv50 of less than 0.5 mm). Dv80 and Dv50 are respectively the particle sizes at the $80^{th}$ and $50^{th}$ percentiles (in volume) of the cumulative size distribution of the Lewis acid particles. These parameters may be determined by sieving. Alternatively, the Lewis acid can also be added as a suspension or a colloid in a solvent. The solvent for the suspension/colloid is advantageously the abovementioned reaction solvent. Alternatively, it can also be added as a solution in a solvent. The solvent for the solution is preferably the abovementioned reaction solvent.

Lewis acids which may be used include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. Aluminum trichloride, boron trichloride, aluminum tribromide, titanium tetrachloride, antimony pentachloride, ferric chloride, gallium trichloride, and molybdenum pentachloride are preferred. Aluminum trichloride is particularly preferred.

In some embodiments, the Lewis acid can be mixed to the starting mixture before adding the second reactant to the starting mixture. In particular, when the first reactant is terephthaloyl chloride, the Lewis acid can be mixed to the starting mixture before adding the diphenyl ether to the starting mixture.

In some embodiments, the Lewis acid can be mixed with the second reactant and added together to the starting mixture. In particular, when the second reactant is terephthaloyl chloride, the Lewis acid can be mixed with terephthaloyl chloride and added together to the starting mixture.

In some embodiments, the Lewis acid can be partly mixed to the starting mixture before adding the second reactant to the starting mixture and, partly mixed with the second reactant and added together to the starting mixture.

In some particular embodiments, the weight concentrations and weight ratios of the reactants and of the catalyst are as follows:
- the concentration of terephthaloyl chloride (relative to the sum of solvent, terephthaloyl chloride, diphenyl ether and Lewis acid introduced into the reactor) is from 2 to 25%, preferably from 3 to 12%, preferably from 5 to 10%;
- the concentration of diphenyl ether (relative to the sum of solvent, terephthaloyl chloride, diphenyl ether and Lewis acid introduced into the reactor) is from 2 to 42%, preferably from 5 to 35%, preferably from 12 to 25%;
- the concentration of Lewis acid (relative to the sum of solvent, terephthaloyl chloride, diphenyl ether and Lewis acid introduced into the reactor) is from 3 to 33%, preferably from 4 to 30%, preferably from 10 to 25%;
- the weight ratio of terephthaloyl chloride to diphenyl ether introduced into the reactor is from 0.05 to 0.6, preferably from 0.2 to 0.6, preferably from 0.3 to 0.5;
- the weight ratio of Lewis acid to terephthaloyl chloride plus diphenyl ether introduced into the reactor is from 0.2 to 0.9, preferably from 0.3 to 0.7.

The addition of the second reactant may preferably be performed progressively, over a period of time which can advantageously range from 5 to 600 minutes, preferably from 30 to 300 minutes.

The addition can be performed continuously or with one or more interruptions. If it is performed continuously, it can be conducted at a constant rate of addition. Alternatively, the rate of addition can vary over time.

The starting mixture is preferably agitated during at least part of the reaction. Thus, the reactor is preferably provided with an agitation device, such as a mechanical stirrer (which may, e.g., comprise one or more impellers) or a recirculation loop with a pump.

Preferably, the starting mixture may be agitated using the agitation device during the addition of other of the two reactants.

The reaction at stake is exothermic. Preferably, a temperature control system is provided, in order to control the temperature of the starting mixture in the reactor, in particular during and after mixing/adding the Lewis acid to the starting mixture and during and after adding the second reactant to the starting mixture. The temperature control system may in particular comprise a temperature sensor within the reactor and may be configured to cool and/or to heat the starting mixture. Preferably, it is at least configured to cool the starting mixture.

Devices for heating and/or cooling the starting mixture may include a heat exchanger inside the reactor or in a recirculation loop, or a heat exchange fluid circuit in the jacket of the reactor.

When the temperature of the starting mixture increases during the step of adding the second reactant, this can be achieved in three different manners:
- by heating the starting mixture (while preferably also controlling the rate of addition of the second reactant, so as to achieve a targeted increase in temperature);
- by simply controlling the rate of addition of the second reactant so as to achieve a targeted increase in temperature, without providing external cooling or heating; or
- by cooling the starting mixture, while also controlling the rate of addition of the second reactant, so as to achieve a targeted increase in temperature.

According to a preferred embodiment, the starting mixture is cooled during and possibly also after the step of adding the second reactant, in order to prevent an excessively large or rapid increase in temperature of the starting mixture as the reactants start reacting with each other.

According to the invention, the temperature of the starting mixture is greater than 5° C. during at least part of the step of adding the second reactant to the starting mixture. In particular variations of embodiments of the invention, the temperature of the starting mixture is at least 10° C., or at least 15° C., or at least 20° C., or at least 25° C., or at least 30° C., or at least 35° C., or at least 40° C., or at least 45° C., or at least 50° C., or at least 55° C., or at least 60° C., or at least 65° C., or at least 75° C., or at least 85° C., or at least 95° C., or at least 100° C., or at least 110° C., or about 120° C., during at least part of the step of adding the second reactant to the starting mixture.

On the other hand, the temperature during the step of adding the second reactant to the starting mixture should preferably remain below a certain threshold, for example, 120° C., in order to avoid any significant polymerization of the reactants into a PEKK polymer.

Furthermore, the temperature during the step of adding the second reactant to the starting mixture should remain below the boiling temperature of the solvent in the operating conditions.

It is possible to operate the reactor in a pressurized manner so that the temperature in the reactor can reach a higher value without causing the solvent to boil. In this case, the pressure in the reactor can range from 1 bar (atmospheric pressure) to 6 bar, preferably from 1.5 bar to 3 bar.

Alternatively, and preferably, the reaction is performed at atmospheric pressure.

According to some variants of embodiments of the invention, the temperature of the starting mixture does not exceed 180° C., preferably does not exceed 120° C., preferably does not exceed 100° C., preferably does not exceed 90° C., more preferably does not exceed 80° C., even more preferably does not exceed 70° C., during the step of adding the second reactant.

It is believed that it is more critical for the temperature of the starting mixture to be relatively high at the end of the step of adding the second reactant than at the beginning of this step, in order to achieve some or all of the advantageous effects of the invention. However, a temperature gradient is not required.

Accordingly, in some variants of embodiments of the invention, once 90% by weight of the second reactant has been added to the starting mixture (relative to the total weight of the second reactant added to the starting mixture), it is preferred that the temperature of the starting mixture is and remains of at least 5° C., preferably at least 10° C., or at least 15° C., or at least 20° C., or at least 25° C., or at least 30° C., or at least 35° C., or at least 40° C., or at least 45° C., or at least 50° C., or at least 55° C., or at least 60° C., or at least 65° C., or at least 75° C., or at least 85° C., or at least 95° C., or at least 100° C., or at least 110° C., or about 120° C., during the remainder of the step of adding the second reactant to the starting mixture.

In some variants of embodiments of the invention, once 75% by weight of the second reactant has been added to the starting mixture (relative to the total weight of the second reactant added to the starting mixture), it is preferred that the temperature of the starting mixture is and remains of at least 5° C., preferably at least 10° C., or at least 15° C., or at least 20° C., or at least 25° C., or at least 30° C., or at least 35° C., or at least 40° C., or at least 45° C., or at least 50° C., or at least 55° C., or at least 60° C., or at least 65° C., or at least 75° C., or at least 85° C., or at least 95° C., or at least 100° C., or at least 110° C., or about 120° C., during the remainder of the step of adding the second reactant to the starting mixture.

In some variants of embodiments of the invention, once 50% by weight of the second reactant has been added to the starting mixture (relative to the total weight of Lewis acid added to the starting mixture), it is preferred that the temperature of the starting mixture is and remains of at least 5° C., preferably at least 10° C., or at least 15° C., or at least 20° C., or at least 25° C., or at least 30° C., or at least 35° C., or at least 40° C., or at least 45° C., or at least 50° C., or at least 55° C., or at least 60° C., or at least 65° C., or at least 75° C., or at least 85° C., or at least 95° C., or at least 100° C., or at least 110° C., or about 120° C., during the remainder of the step of adding the second reactant to the starting mixture.

In some variants of embodiments of the invention, once 20% by weight of the second reactant has been added to the starting mixture (relative to the total weight of the second of the two reactants added to the starting mixture), it is preferred that the temperature of the starting mixture is and remains of at least 5° C., preferably at least 10° C., or at least 15° C., or at least 20° C., or at least 25° C., or at least 30° C., or at least 35° C., or at least 40° C., or at least 45° C., or at least 50° C., or at least 55° C., or at least 60° C., or at least 65° C., or at least 75° C., or at least 85° C., or at least 95° C., or at least 100° C., or at least 110° C., or about 120° C., during the remainder of the step of adding the second reactant to the starting mixture.

The temperature of the starting mixture can remain constant during the step of adding the second reactant. Alternatively, it can vary during this step.

By "initial temperature" is meant the temperature of the starting mixture at the beginning of the step of adding the second reactant, i.e., as the first molecules of the second reactant are added to the starting mixture.

By "final temperature" is meant the temperature of the starting mixture at the end of the step of adding the second reactant, i.e., as the last molecules of the second reactant are added to the starting mixture.

The initial temperature of the starting mixture may range from, e.g., −30° C. to 120° C. In some variations, the initial temperature of the starting mixture is from −30 to −25° C.; or from −25 to −20° C.; or from −20 to −15° C.; or from −15 to −10° C.; or from −10 to −5° C.; or from −5 to −0° C.; or from 0 to 5° C.; or from 5 to 10° C.; or from 10 to 15° C.; or from 15 to 20° C.; or from 20 to 25° C.; or from 25 to 30° C.; or from 30 to 35° C.; or from 35 to 40° C.; or from 40 to 45° C.; or from 45 to 50° C.; or from 50 to 55° C.; or from 55 to 60° C.; or from 60 to 65° C.; or from 65 to 70° C.; or from 70 to 75° C.; or from 75 to 80° C.; or from 80 to 85° C.; or from 85° C. to 90° C.; or from 90° C. to 100° C.; or from 100° C. to 110° C.; or from 110° C. to 120° C. Ranges of from 0 to 80° C., more particularly from 20 to 50° C. are preferred.

The final temperature of the starting mixture may range from, e.g., 10° C. to 120° C. In some variations, the final temperature of the starting mixture is from 10 to 15° C.; or from 15 to 20° C.; or from 20 to 25° C.; or from 25 to 30° C.; or from 30 to 35° C.; or from 35 to 40° C.; or from 40 to 45° C.; or from 45 to 50° C.; or from 50 to 55° C.; or from 55 to 60° C.; or from 60 to 65° C.; or from 65 to 70° C.; or from 70 to 75° C.; or from 75 to 80° C.; or from 80 to 85° C.; or from 85° C. to 90° C.; or from 90° C. to 100° C.; or from 100° C. to 110° C.; or from 110° C. to 120° C. Ranges of from 30 to 80° C., and more particularly from 40 to 70° C., even more particularly from 45 to 60° C. are preferred. In some variations, the final temperature is at least 30° C., preferably at least 40° C., more preferably at least 45° C. and most preferably at least 50° C.

In some variations, the temperature of the starting mixture decreases during the step of adding the second reactant, i.e. the final temperature is lower than the initial temperature.

In preferred variations, the temperature of the starting mixture increases during the step of adding the second reactant, i.e., the final temperature is greater than the initial temperature.

In some embodiments, the temperature difference ΔT between the final temperature and the initial temperature is from 1 to 120° C., preferably from 1 to 70° C., preferably from 5 to 60° C., more preferably from 10 to 50° C., and in particular from 20 to 40° C.

In some variations of embodiments of the invention, the increase in temperature is monotonous, i.e. there is no transient decrease in temperature during the entire step of adding the second reactant. On the other hand, transient variations or fluctuations in temperature are possible in some embodiments, especially due to the non-instantaneous nature of the temperature control.

In some variations, the temperature of the starting mixture continuously increases from the initial temperature to the final temperature. Alternatively, the temperature of the starting mixture may comprise one or more increase stages and one more plateau stages during the step of adding the second reactant. In particular, the temperature of the starting mixture may initially increase during a first part of the step of adding the second reactant, from the initial temperature to the final temperature, and then plateau at the final temperature during a second part of the step of adding the second reactant. In this case, the plateau temperature may be set with a precision of, e.g., +/−5° C., or +/−2° C., or +/−1° C.

Once the step of adding the second reactant to the starting mixture is complete, the mixture can optionally be maintained, preferably under agitation, for a certain time, in order to complete the reaction to the desired degree. Preferably, the mixture is maintained from 0 to 600 min, more preferably from 5 to 180 min.

There is no limitation as to the temperature of the mixture during this step of maintaining. In some variations of embodiments of the invention, the temperature of the mixture is maintained at the final temperature described above. In other variations, it increases or decreases relative to the final temperature.

Once the reaction is completed to the desired degree, the mixture becomes designated as a product mixture.

The method of embodiments of the invention advantageously comprises one or more steps for purifying the 1,4-bis(4-phenoxybenzoyl)benzene-Lewis acid complex from the product mixture, and in particular from the reaction solvent, catalyst and unreacted reactants as well as by-products.

The 1,4-bis(4-phenoxybenzoyl)benzene-Lewis acid complex can be put in contact with a decomplexing solvent, the decomplexing solvent being a protic solvent, so as to dissociate the phenoxybenzoyl)benzene-Lewis acid complex into 1,4-bis(4-phenoxybenzoyl)benzene, which is at least partly in the form of a precipitate in the decomplexing solvent, and into a derivative of Lewis acid which is mostly solubilized in the decomplexing solvent under a form depending on the nature of the decomplexing solvent. For example, the derivative of Lewis acid can be under the form of a ionic salt, metal hydroxides and their counter-ions, metal alcoxides and their counter-ions or any other compound(s) resulting from the reaction of the Lewis acid with the decomplexing solvent.

The decomplexing solvent is advantageously selected so that 1,4-bis(4-phenoxybenzoylbenzene) tends to precipitate. The decomplexing solvent can be an organic solvent, such as methanol, acetic acid, formic acid, ethanol, isopropanol, and benzyl alcohol. Alternatively, the decomplexing solvent can be an aqueous solution, such as a solution of hydrochloric acid. Mixtures of the above solvents can also be used, such as an aqueous-organic solvent, e.g., an aqueous solution mixed with methanol.

In specific embodiments, the purification may comprise the steps of:
mixing the product mixture with a decomplexing solvent, being a protic solvent, so as to provide a product slurry;
separating 1,4-bis(4-phenoxybenzoylbenzene) from the product slurry, preferably by filtration and washing.

By way of example, methanol may be used as a decomplexing solvent. Alternatively, a solution of hydrochloric acid may also be used as a decomplexing solvent.

The desired product can then be recovered from the product slurry by filtration. If necessary, the desired product can be further purified by methods well-known by the skilled person such as being submitted to washing step(s), and/or recrystallization step(s) and/or distillation step(s) to eliminate or reduce the amount of remaining impurities. In particular, the product can be washed, preferably by a protic solvent such as methanol, and filtrated again, once or several times. Washing can be performed for example by re-slurrying the product in the solvent.

The 1,4-bis(4-phenoxybenzoyl)benzene obtained according to embodiments of the invention can subsequently be used to perform a polymerization reaction so as to make a polyaryletherketone polymer (PAEK). In particular, the 1,4-bis(4-phenoxybenzoyl)benzene obtained according to embodiments of the invention can subsequently be used to perform a polymerization reaction so as to make a polyetherketoneketone polymer (PEKK).

In order to make the PAEK, 1,4-bis(4-phenoxybenzoyl)benzene is reacted with at least one difunctional aromatic acyl chloride.

The difunctional aromatic acyl chloride may be chosen among the list consisting of: terephthaloyl chloride, isophthaloyl chloride, phthaloyl chloride, phosgene, adipoyl dichloride, tetrabromophthaloyl chloride, compounds of the following formula and mixtures thereof:

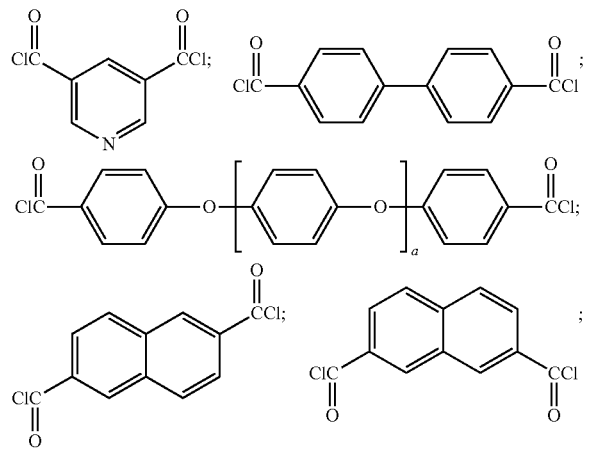

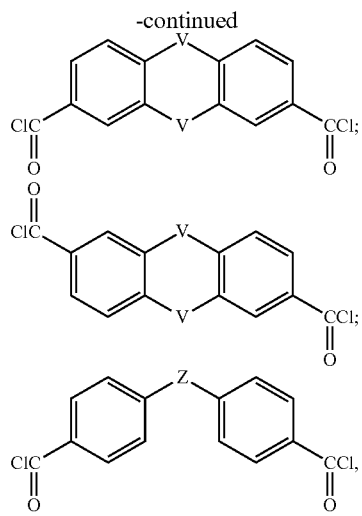

wherein:
a is an integer between 0 to 3;
V is chosen among: —O—, —S—, —N=N—, —(CF$_2$)$_q$—, —(CH$_2$)$_q$—, or —C((CH$_3$)$_2$)—;
Z is chosen among —C(O)—, —SO$_2$—, —C(O)—C$_6$H$_4$—C(O)—, —O—(CF$_2$)$_q$—O—, —S—, —N=N—, —(CF$_2$)$_q$—, —(CH$_2$)$_q$—, or C—(CH$_3$)$_2$—; and,
wherein q is an integer between 1 to 20.

In the embodiment in which the PAEK is PEKK, the difunctional aromatic acyl chloride can be a mixture of phthaloyl chloride, terephthaloyl chloride, and isophthaloyl chloride. Preferably, the difunctional aromatic acyl chloride is a mixture of terephthaloyl chloride and isophthaloyl chloride.

The reaction is preferably implemented in a solvent. The solvent is preferably a non-protic solvent, which can in particular be selected from methylene chloride, carbon disulfide, ortho-dichlorobenzene, meta-dichlorobenzene, para-dichlorobenzene, 1,2,4-trichlorobenzene, ortho-difluorobenzene, 1,2-dichloroethane, 1,1-dichloroethane, 1,1,2,2-tetrachloroethane, tetrachloroethylene, dichloromethane, nitrobenzene and mixtures thereof.

The reaction is preferably implemented in the presence of a Lewis acid as a catalyst.

Lewis acids which may be used include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. Aluminum trichloride, boron trichloride, aluminum tribromide, titanium tetrachloride, antimony pentachloride, ferric chloride, gallium trichloride, and molybdenum pentachloride are preferred. Aluminum trichloride is particularly preferred.

The polymerization can be implemented in the same reactor as the one used for the production of 1,4-bis(4-phenoxybenzoyl)benzene. But more preferably it is implemented in one or more other reactors.

The polymerization can be carried out at a temperature ranging from, e.g., 20 to 120° C.

The method of making the PAEK polymer, and in particular PEKK, advantageously also comprises one or more steps for purifying the PAEK polymer, such as steps of:
mixing the mixture containing the PAEK polymer with a protic solvent so as to provide a PAEK slurry;

separating the PAEK polymer from the PAEK slurry, preferably by filtration and washing.

The protic solvent used to make the PAEK slurry may be, e.g., methanol.

The PAEK polymer can then be recovered from the PAEK slurry by filtration. If necessary, the polymer can be washed, preferably by a protic solvent such as methanol, and filtrated again, once or several times. Washing can be performed for example by re-slurrying the polymer in the solvent.

EXAMPLES

The following examples illustrate embodiments of the invention without limiting it.

Example 1 (Comparative)

In a 250 mL reactor equipped with a magnetic stirrer, with a nitrogen inlet and outlet going to a scrubber system, 157 g of ortho-dichlorobenzene, 17.3 g of terephthaloyl chloride and 42.9 g of diphenyl ether were introduced at 25° C.

After full solubilization, 35.3 g of AlCl$_3$ were slowly added to the reactant mixture during 90 min between 25 to 50° C. After completion of AlCl$_3$ addition, the mixture was kept agitated at 50° C. during 3 hours to finish the reaction. Then the mixture was quenched in 3 wt. % acidic aqueous solution. After removal of aqueous aluminic phase, a sample of product slurry was analyzed with 1H NMR. Molar ratios for the three following species: 1,4-bis(4-phenoxybenzoyl) benzene (desired product), xanthydrol moiety-containing molecules (by-product) and 4-(4-phenoxybenzoyl)benzoic acid) (by-product) was calculated based on the characteristic peaks of the relevant species.

They were expressed as follows for each species:

Molar ratio [species]=[Mol %[species]/Σ(Mol % EKKE+Mol % xanthydrol moiety-containing molecules+Mol % 4-(4-phenoxybenzoyl)benzoic acid)]×100.

Examples 2-4 (Invention)

Experiments analogous to example 1 were performed but with an addition at 25° C. of the chemicals in a different sequence.

In examples 2, 3 and 4, terephthaloyl chloride was added to a starting mixture comprising ortho-dichlorobenzene and diphenyl ether.

Example 2 was performed by a simultaneous addition at 25° C. of terephthaloyl chloride and AlCl$_3$ both at solid states to the starting mixture consisting of ortho-dichlorobenzene and diphenyl ether.

Example 3 was performed by addition at 25° C. of terephthaloyl chloride at solid state to the starting mixture consisting of ortho-dichlorobenzene, diphenyl ether and AlCl$_3$.

Example 4 was performed by addition at 25° C. of terephthaloyl chloride in a solution of ortho-dichlorobenzene to the starting mixture consisting of ortho-dichlorobenzene, diphenyl ether and AlCl$_3$.

Table 1 below summarizes the results obtained for examples 1-4, in terms of ratio of 1,4-bis(4-phenoxybenzoyl)benzene (yield) and ratio of two kinds of by-products: xanthydrol moiety-containing molecules and 4-(4-phenoxybenzoyl)benzoic acid.

TABLE 1

| Example No. | 1 | 2 | 3 | 4 |
|---|---|---|---|---|
| Molar ratio 1,4-bis(4-phenoxybenzoyl)benzene | 95.1 | 95.2 | 95.1 | 95.2 |
| Molar ratio xanthydrol moiety-containing molecules | 4.8 | 4.7 | 4.9 | 4.8 |
| Molar ratio 4,(4-phenoxybenzoyl)benzoic acid | 0.09 | 0.03 | 0.03 | 0.04 |

Changing the sequence of addition of the chemicals enable to obtain 1,4-bis(4-phenoxybenzoyl)benzene having slightly less or around the same amount of xanthydrol moiety-containing molecules and 4,(4-phenoxybenzoyl) benzoic acid (examples 2-4 (invention) in comparison with example 1 (comparative)).

The invention claimed is:

1. A method for manufacturing 1,4-bis(4-phenoxybenzoyl)benzene, comprising:
   providing a solvent, a Lewis acid, a first reactant and a second reactant, wherein the first reactant and the second reactant are respectively terephthaloyl chloride and diphenyl ether, or reversely; and wherein the solvent is a separate solvent from the first reactant, the second reactant and the Lewis acid;
   mixing the first reactant in the solvent to make a starting mixture; and,
   adding the second reactant to the starting mixture;
   wherein the Lewis acid is mixed, at least partly, to the starting mixture before adding the second reactant to the starting mixture, and/or
   wherein the Lewis acid is mixed, at least partly, with the second reactant and added together to the starting mixture, and
   wherein the temperature of the starting mixture is greater than 5° C. during at least part of the step of adding the second reactant to the starting mixture;
   so as to obtain a product mixture comprising a 1,4-bis(4-phenoxybenzoyl)benzene-Lewis acid complex,
   wherein the Lewis acid is chosen among the list consisting of: aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride.

2. The method of claim 1, wherein the Lewis acid is chosen among the list consisting of: aluminum trichloride, boron trichloride, aluminum tribromide, titanium tetrachloride, antimony pentachloride, ferric chloride, gallium trichloride, and molybdenum pentachloride.

3. The method of claim 2, wherein the Lewis acid is aluminum trichloride.

4. The method of claim 1, wherein the temperature of the starting mixture is at least 15° C. during at least part of the step of adding the second reactant to the starting mixture.

5. The method of claim 1, wherein the temperature of the starting mixture is at least 30° C. after 20% by weight of the second reactant has been added to the starting mixture, relative to the total weight of the second reactant added to the starting mixture.

6. The method of claim 1, wherein the temperature of the starting mixture increases during the step of adding the second reactant to the starting mixture, from an initial temperature to a final temperature.

7. The method of claim 6, wherein the initial temperature of the starting mixture is from 0° C. to 120° C.

8. The method of claim 6, wherein the final temperature of the starting mixture is at least 30° C.

9. The method of claim 1, wherein the temperature of the starting mixture does not exceed 180° C. during the step of adding the second reactant.

10. The method of claim 1, wherein the solvent is ortho-dichlorobenzene.

11. The method of claim 1, wherein the second reactant is terephthaloyl chloride and, wherein the Lewis acid is mixed with terephthaloyl chloride and added together to the starting mixture.

12. The method of claim 1, wherein the first reactant is terephthaloyl chloride and, wherein the Lewis acid is mixed with the starting mixture before adding the diphenyl ether to the starting mixture.

13. The method of claim 1, wherein the concentration by weight of terephthaloyl chloride (relative to a sum by weight of the solvent, the terephthaloyl chloride, the diphenyl ether and the Lewis acid) is from 2 to 25%.

14. The method of claim 1, wherein the concentration by weight of diphenyl ether (relative to a sum by weight of the solvent, the terephthaloyl chloride, the diphenyl ether and the Lewis acid) is from 2 to 42%.

15. The method of claim 1, wherein the weight ratio of terephthaloyl chloride to diphenyl ether introduced into the reactor is from 0.05 to 0.6.

16. A method of making a polyaryletherketone polymer, comprising:
   manufacturing 1,4-bis(4-phenoxybenzoyl)benzene according to the method of claim 1;
   reacting said 1,4-bis(4-phenoxybenzoyl)benzene with at least one difunctional aromatic acyl chloride.

\* \* \* \* \*